United States Patent
Somani et al.

(10) Patent No.: US 11,779,541 B2
(45) Date of Patent: Oct. 10, 2023

(54) IMMEDIATE RELEASE DOSAGE FORM

(71) Applicant: Johnson & Johnson Consumer Inc., Skillman, NJ (US)

(72) Inventors: Jitendra Krishan Somani, Waterloo (CA); Murali K. Vuppala, Collegeville, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/364,244

(22) Filed: Mar. 26, 2019

(65) Prior Publication Data
US 2020/0306192 A1   Oct. 1, 2020

(51) Int. Cl.
*A61K 9/20* (2006.01)
*A61K 9/28* (2006.01)
*A61K 31/192* (2006.01)

(52) U.S. Cl.
CPC .......... *A61K 9/2009* (2013.01); *A61K 9/2013* (2013.01); *A61K 9/2027* (2013.01); *A61K 9/2054* (2013.01); *A61K 9/2059* (2013.01); *A61K 9/284* (2013.01); *A61K 31/192* (2013.01)

(58) Field of Classification Search
None
See application file for complete search history.

(56) References Cited

U.S. PATENT DOCUMENTS

| | | | | |
|---|---|---|---|---|
| 5,693,312 A * | 12/1997 | Stroppolo | ............ | A61K 9/0007 424/44 |
| 6,165,506 A | 12/2000 | Jain et al. | | |
| 6,328,994 B1 | 12/2001 | Shimizu et al. | | |
| 6,713,089 B1 * | 3/2004 | Bertelsen | ............ | A61K 9/1611 424/464 |
| 7,431,942 B2 * | 10/2008 | Shimizu | ............... | A61K 9/0056 424/466 |
| 9,757,455 B2 | 9/2017 | Roberts et al. | | |
| 2003/0040537 A1 * | 2/2003 | Plachetka | ............ | A61K 9/0007 514/406 |
| 2007/0134317 A1 | 6/2007 | Gruber et al. | | |
| 2009/0142392 A1 | 6/2009 | Sherry | | |
| 2009/0311327 A1 | 12/2009 | Roberts et al. | | |
| 2012/0148634 A1 | 6/2012 | Dodd et al. | | |
| 2014/0037725 A1 * | 2/2014 | Kannan | ................ | A61K 9/2054 424/465 |
| 2015/0010638 A1 | 1/2015 | Sakuma et al. | | |

OTHER PUBLICATIONS

Davies et al., "Clinical Pharmacokinetics of Naproxen", *Clinical Pharmacokinetcs* (1997) 32(4):268-293.
Lieberman et al., *Pharmaceutical Dosage Forms—Tables*, vol. 2, 2nd ed., Marcel Dekker Inc., 1990, pp. 213-217 and 327-329.
Setiawati et al., "Bioequivalence Study with Two Naproxen Sodium Tablet Formulations in Health Subjects", *Journal of Bioequivalence & Bioavailability* (2009) 1(1):28-33.
USP 28, Physical Tests, Section 701 Disintegration, US Pharmacopeial Convention, Inc. meeting at Washington, DC Apr. 12-16, 2000, Official from Jan. 1, 2005, pp. 2411-2412.
Product monograph Aleve Liquid Gels Naproxen Sodium Tablets USP 220 mg Non-steroidal anti-inflammatory drug Analgesic, Antipyretic, Bayer Inc. Consumer Care, Apr. 10, 2013. Control No. 162299.
International Search Report dated Jun. 24, 2020, for international application PCT/IB2020/052374.
Bochkov et al., "Factors, effecting on drug bioavailability", Pharmacokinetics and Pharmacodynamics 2016 1:12-19.
Rowe et al., Handbook of Pharmaceutical Excipients, Fifth Edition, 2006, pp. 91, 423, 665.

\* cited by examiner

*Primary Examiner* — Celeste A Roney

(57) ABSTRACT

An improved immediate release solid dosage form of naproxen with a certain particle size distribution for the intragranular portion, and a certain particle size distribution for the carbonate portion that allows naproxen to remain in solution and achieves fast dissolution and fast absorption of naproxen. The invention provides a naproxen dosage form that when administered to a human in a fasted state provides an average blood plasma naproxen concentration of at least 15-20 μg/ml in 10 minutes or less. The invention also provides a naproxen dosage form that when administered to a human in a fed state provides an average blood plasma naproxen concentration of at least 15-20 μg/ml in 50 minutes or less.

10 Claims, 2 Drawing Sheets

IMMEDIATE RELEASE DOSAGE FORM

The present invention relates to a novel immediate release solid dosage form which achieves fast dissolution and fast absorption of naproxen in humans.

BACKGROUND OF INVENTION

Naproxen is a propionic acid derivative. It is a nonsteroidal anti-inflammatory drug and a potent inhibitor of the cyclooxygenase responsible for the biosynthesis of prostaglandins Naproxen has anti-inflammatory, analgesic and antipyretic activity in man. Naproxen and salts of naproxen are indicated for the reduction of fever and the treatment of pain, e.g. arthritis pain, pain of inflammation, muscular ache, backache, headache, migraine pain, pain of menstrual cramps, toothache, and pains associated with common cold.

Davies and Anderson, *Clinical Pharmacokinetics,* 32(4): 268-93 (1997) reports that following oral administration, naproxen is rapidly and completely absorbed, and the extent of absorption results in similar exposure, as measured by area under the concentration-time curve, compared with intravenous administration. The rapidity but not the extent of absorption is affected by the presence of food in the stomach. Maximum plasma concentration is typically achieved within 1-2 hours after administration of naproxen sodium.

Speed to the onset of pain relief is an important unmet need in the pain care space. Improving the rate and extent of absorption of oral formulations of compounds has been and continues to be researched. Once an immediate release solid swallow composition reaches the stomach, it undergoes disintegration and/or dissolution and passes into the small intestine where the active ingredient is absorbed across the intestinal walls into the circulatory system via the portal vein and liver before reaching the site of action. For drugs where absorption is not rate limited, such as naproxen, fast disintegration and fast dissolution of the active ingredient will promote fast absorption in vivo. U.S. Pat. No. 9,757,455 (Roberts et. al) discloses formulations manufactured as immediate release solid dosage forms intended to be swallowed intact, which achieve fast dissolution and fast absorption of an active ingredient, including naproxen.

However, naproxen does have pH related solubility. In pH above 5.4, naproxen stays in solution. At lower acidic pH conditions, naproxen sodium dissolves but immediately precipitates out into a fine colloidal particulate matter of naproxen. If naproxen precipitates in the stomach, the naproxen must pass into the small intestine before it solubilizes and re-dissolves. This may create a delay in absorption.

Patent application publication US20070134317 describes this phenomenon and discloses a non-effervescent form of sodium naproxen comprising sodium hydrogen carbonate. It describes the formation of agglomerates of precipitated naproxen to larger, poorly soluble naproxen crystal agglomerates, and proposes formulations to minimize potential poor solubility and bioavailability.

Applicants have now discovered an improved immediate release solid dosage form with a certain particle size distribution for the intragranular portion, and a certain particle size distribution for the carbonate portion which allows for naproxen to remain in solution and achieves faster dissolution and faster absorption of naproxen in humans. In particular, applicants have discovered a naproxen dosage form that when administered to a human in a fasted state provides an average blood plasma naproxen concentration of at least 15-20 µg/ml in 10 minutes or less. Applicants have further discovered a naproxen dosage form that when administered to a human in a fed state provides an average blood plasma naproxen concentration of at least 15-20 µg/ml in 50 minutes or less for compositions comprising 300 mg to 500 mg of a carbonate compound. Applicants have further discovered a naproxen dosage form that when administered to a human in a fed state provides an average blood plasma naproxen concentration of at least 15-20 µg/ml in 25 minutes or less for compositions comprising 500 mg of a carbonate compound.

SUMMARY OF THE INVENTION

The present invention provides an improved immediate release solid dosage form of naproxen sodium that achieves fast dissolution in the stomach, allows naproxen to remain in solution and achieves fast absorption of naproxen. Particularly, the present invention provides a naproxen sodium dosage form that when administered to a human in a fasted state provides an average blood plasma naproxen concentration of at least 15-20 µg/ml in 10 minutes or less. The present invention also provides a naproxen dosage form that when administered to a human in a fed state provides an average blood plasma naproxen concentration of at least 15-20 µg/ml in 50 minutes or less for compositions comprising 300 mg to 500 mg of a carbonate compound. The present invention also provides a naproxen dosage form that when administered to a human in a fed state provides an average blood plasma naproxen concentration of at least 15-20 µg/ml in 25 minutes or less for compositions comprising 500 mg of a carbonate compound.

In one embodiment, the immediate release solid dosage form of naproxen sodium has an intragranular particle size distribution of about 200-400 microns. In another embodiment, the immediate release solid dosage form of naproxen has a carbonate particle size distribution of about 50-200 microns.

BRIEF DESCRIPTION OF THE DRAWINGS

The drawings described herein are for illustrative purposes only of selected embodiments, and are not intended to limit the scope of the present disclosure.

DETAILED DESCRIPTION OF EMBODIMENTS OF THE INVENTION

Figure 1:
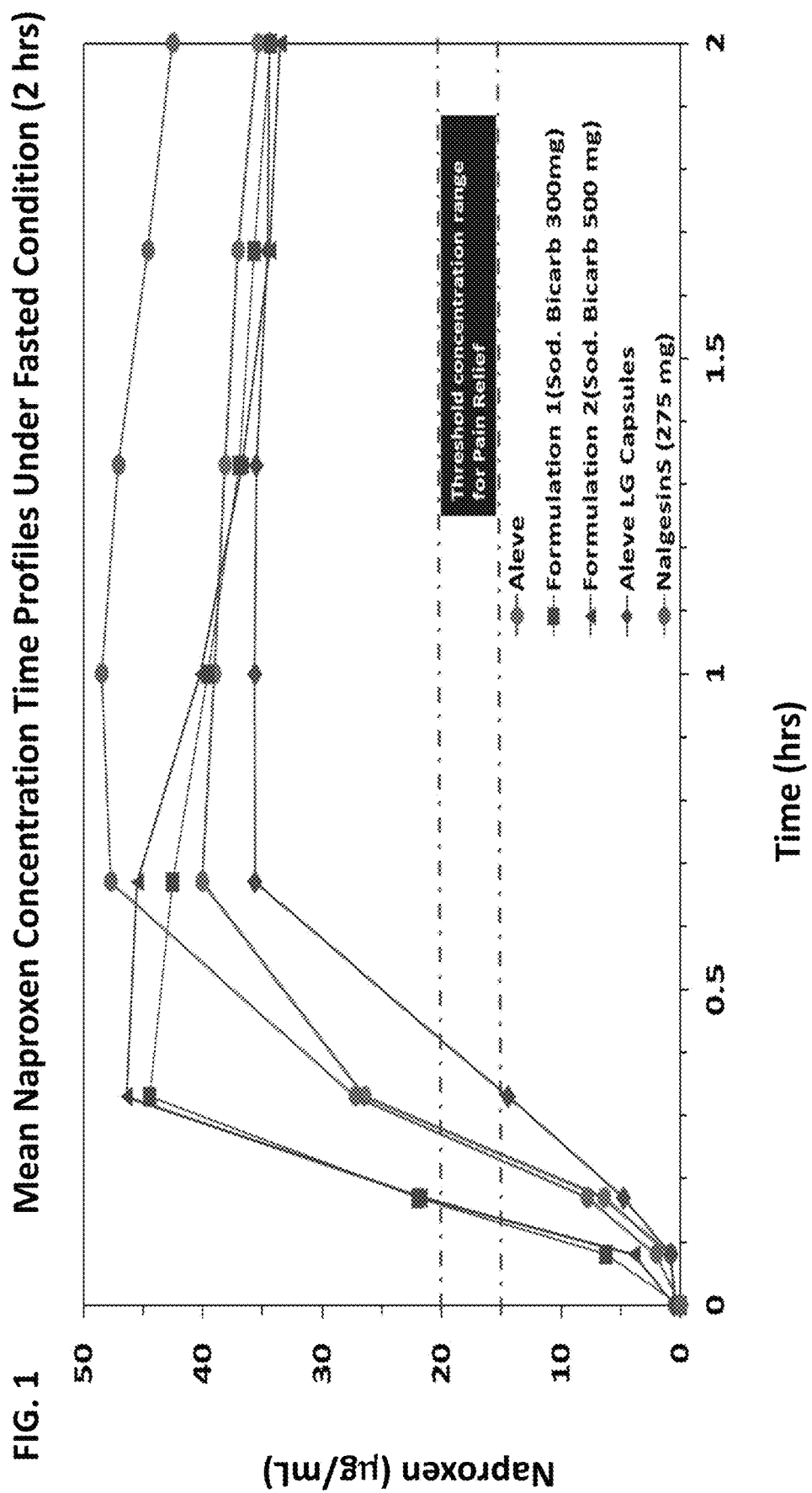
FIG. 1 depicts the mean naproxen concentration time profiles under fasted conditions for the study described in Examples 1 and 2.

The present invention is directed to the use of a composition which delivers a time to a specific average blood plasma (therapeutic) concentration in mammalian subjects which correlates to pain relief. This minimum effective therapeutic plasma concentration (MEC) for naproxen is defined herein as between 15 to 20 µg/mL. In one embodiment this is regarded as administration in a fasted condition with a resulting time to the MEC of a range of 7 minutes to 9 minutes. In one embodiment the time to MEC in a fasted condition is less than 20 minutes, or less than 15 minutes, or less than 10 minutes. In another embodiment the time to minimum effective therapeutic concentration in a fed condition is in a range of 15 minutes to 25 minutes. In another embodiment, the time to MEC in a fed condition is less than 50 minutes, or less than 40 minutes, or less than 35 minutes, or less than 30 minutes, or less than 25 minutes, or less than 20 minutes.

The present invention can be further defined as the time to maximum plasma concentration. In one embodiment the time to maximum plasma concentration is less than 35 minutes, or less than 30 minutes or less than 25 minutes.

The composition of the present invention contains an intragranular portion and an extragranular portion. The intragranular portion may contain naproxen sodium, compression fillers, binders and disintegrants. Compressible fillers include but are not limited to microcrystalline cellulose, directly compressible microcrystalline cellulose, celluloses, water insoluble celluloses, starch, cornstarch and modified starches. Suitable fillers include but are not limited to starch and modified starches. The filler may be added at a range of about 5 percent to about 50 percent, or from about 10 percent to about 40 percent by weight of the tablet. Suitable disintegrants include, but are not limited to, sodium starch glycolate, cross-linked polyvinylpyrrolidone, cross-linked carboxymethylcellulose, starches, microcrystalline cellulose, and mixtures thereof. Disintegrants may be added at a range from about 0.5 percent to about 15 percent, or from about 1 percent to about 10 percent by weight of the tablet. In one embodiment the disintegrant is added in the intragranular portion at a range of from about 1 percent to about 3 percent and in the extragranular portion at a range from about 5 percent to about 9 percent by total weight of the tablet.

Extragranular materials include carbonates, compression fillers, lubricants, flow aids, and disintegrants. Suitable carbonates include potassium bicarbonate and sodium bicarbonate. Suitable lubricants include magnesium stearate and stearic acid. The lubricant or flow aid may be added at a range of from about 0.1 percent to about 5.0 percent, of from about 0.1 percent to about 2.0 percent by weight of the tablet. Suitable flow aids include silicon dioxide. In certain embodiments, the tablet comprises less than 0.75 percent magnesium stearate, or less than 0.5 percent magnesium stearate. In one embodiment the compression filler in the extragranular portion is microcrystalline cellulose. In this embodiment the microcrystalline cellulose has a mean particle size of less than 50 microns, or less than 30 microns.

In one embodiment the extragranular portion comprises a "pH modulating agent" and includes one or more than one pH modulating agents which alter the pH of an aqueous solution. These may include acids, bases or a combination of one or more acids and/or bases.

The carbonate may be any pharmaceutically acceptable soluble carbonate or a mixture thereof and includes bicarbonate. Reference to a "bicarbonate" or a "carbonate" includes a single agent or multiple (i.e. two or more) agents. Preferred carbonates include but are not limited to sodium bicarbonate, sodium carbonate, potassium bicarbonate, potassium carbonate, calcium bicarbonate, calcium carbonate, magnesium bicarbonate, magnesium carbonate, ammonium bicarbonate, ammonium carbonate, sodium glycine carbonate, disodium glycine carbonate, arginine carbonate, lysine carbonate and/or other pharmaceutically acceptable carbonates or homologs or functional equivalents thereof and combinations thereof. The carbonate may be added at a range of from about 20 percent to about 50 percent, or from about 25 percent to about 45 percent by weight of the tablet. In one embodiment the intragranular portion is substantially free of the carbonate. By substantially free, as used herein, the intragranular portion comprises less than 0.1 percent of carbonate by weight of the tablet.

The carbonates of the present invention have a mean particle size range of from about 50 microns to about 200 microns, or from about 75 microns to about 100 microns. The particle size of the carbonate portion of the present invention contributes to the dissolution of the composition. It was found that the higher the particle size of the carbonate, the slower the dissolution profile of the composition.

The intragranular portion of the present invention also comprises physical characteristics which contribute to the dissolution of the composition. In one embodiment the mean particle size of the intragranular portion is from about 200 microns to about 400 microns, or from about 200 microns to about 300 microns.

Naproxen sodium has pH related solubility. In pH above 5.4, naproxen sodium stays in solution. At lower acidic pH, naproxen sodium dissolves but immediately precipitates out into a fine colloidal particulate matter. If the naproxen precipitates in the stomach, the naproxen must pass into the small intestine before it re-dissolves creating a delay in absorption. The particle size of the intragranular and carbonate portions of the invention help keep the active ingredient naproxen in solution as it dissolves in the acidic pH of the stomach. The carbonate portion of the dosage form dissolves at a rate such that it raises the pH of the milieu in the micro and macro environment of the stomach which facilitates the dissolution of naproxen and allows the naproxen to remain in solution and allows absorption of naproxen to begin in the stomach.

In certain embodiments bulk density of the intragranular portion is from about 0.5 to about 0.9 g/cc, or from about 0.5 to about 0.7 g/cc. In certain embodiments, the tablet of the present invention is compressed at specific compression force ranges, including from about 18 kilonewtons to about 26 kilonewtons, for a hardness of from about 10 kiloponds to about 17 kiloponds. In embodiments where 300 mg of bicarbonate is incorporated into the tablet blend, the tablet comprises a hardness of about 10 kiloponds to about 16 kiloponds. In embodiments where 500 mg of carbonate is used, the tablet comprises a hardness of about 11 kiloponds to about 17 kiloponds.

Hardness is a term used in the art to describe the diametral breaking strength as measured by conventional pharmaceutical hardness testing equipment, such as a Schleuniger Hardness Tester. In order to compare values across different size tablets, the breaking strength must be normalized for the area of the break. This normalized value, expressed in kp/cm2, is sometimes referred in the art as tablet tensile strength. A general discussion of tablet hardness testing is found in Leiberman et al., Pharmaceutical Dosage Forms—Tablets, Volume 2, 2.sup.nd ed., Marcel Dekker Inc., 1990, pp. 213-217, 327-329.

In other embodiments the tablets of the present invention disintegrate in water. In this case the disintegration time is measured using the Disintegration test and apparatus in USP 28, Section 701 using deionized water at 37° C. The disintegration time for tablets of the present invention are less than 3 minutes, or less than 2 minutes and 30 seconds. In other embodiments the granulation (intragranular portion) is granulated and passed as a wet material through a mill prior to drying. In other embodiments, the dosage form may be a tablet, capsule, powder or other unit presentation. These dosage forms may also comprise an intragranular and extragranular portion.

Preferably, the carbonate is present in an amount from about 1% to about 75% by weight of swallow formulation and in an amount that will neutralise between about 0.01 and 10 millimoles of hydrochloric acid. More preferably the carbonate is present in an amount from about 10% to about 70% by weight in the swallow formulation and in an amount that will neutralise between about 0.02 and 8 millimoles of hydrochloric acid. The carbonate component of the pH modulating agent is present in an amount from about 1 mg to about 500 mg in the swallow formulation, or from about 300 mg to 500 mg. Examples of other particular amounts of carbonate include 8 to 850 mg per swallow formulation. More preferably the carbonate is present in an amount from about 15 mg to 700 mg.

In one swallow formulation embodiment, the carbonate is sodium bicarbonate and/or potassium bicarbonate and is present in an amount from about 5% to 75% by weight of the swallow formulation.

The water uptake agent may be present in an amount from 5% to 95%, or 10% to 90% or more preferably from 20% to 60% by weight of the swallow formulation and more preferably between 30% and 50% by weight of the swallow formulation.

Preferably, the ratio of water uptake agent to pH modulating agent is between 0.1:1 and 20:1. More preferably the ratio of water uptake agent to pH modulating agent is between 0.3:1 and 15:1 or even more preferably between 0.5:1 and 8:1 by weight.

Typically, at least 50% of the therapeutic compound is dissolved from the swallow formulation within 300 seconds in USP dissolution apparatus 2 with 900 mL 0.0033 N hydrochloric acid at 30 rpm and 37° C. In a preferred embodiment at least 55% of the therapeutic compound is dissolved from the swallow formulation within 300 seconds in USP dissolution apparatus 2 with 900 mL 0.0033 N hydrochloric acid at 30 rpm and 37° C. In another embodiment, at least 50% is dissolved in 240 seconds. In another embodiment, at least 75% is dissolved from the swallow formulation within 180 seconds in USP dissolution apparatus 2 with 900 mL of pH 7.4 phosphate buffer at 50 rpm and 37° C. In a preferred embodiment at least 95% is released within 300 seconds in USP dissolution apparatus 2 with 900 mL of pH 7.4 phosphate buffer at 50 rpm and 37° C.

Example 1: Protocol for Naproxen Pharmacokinetic (PK) Evaluation

Methodology:

This study which was conducted was an open-label, single-dose, randomized, crossover study design conducted in three parts and five separate treatment periods. Thirty healthy subjects, ages 18 to 55 years were enrolled. No less than approximately 40% of either gender were represented in the study population.

Part 1 of the study was a fasted, three-way crossover design in which all subjects were randomized to six sequences of Treatments A, B and C over consecutive periods, combined with one of treatments D and E in Part 2, and one of treatments F, G and H in part 3.

In Part 1, the treatments consisted of a single dose of naproxen sodium as test 220 mg tablet formulation 1 (Treatment A), test 220 mg tablet formulation 2 (Treatment B) and Aleve® 220 mg tablet (Treatment C), that were administered with approximately 240 mL water after an overnight fast of at least 10 hours.

In Part 2, the treatments were a single dose of naproxen sodium as Nalgesin S® 275 mg tablet (Treatment D) or Aleve 220 mg Liquid Gels® (Treatment E). In Part 3, the treatments were a single dose of naproxen sodium as test 220 mg tablet formulation 1 (Treatment F), test 220 mg tablet formulation 2 (Treatment G), or Aleve® 220 mg tablet (Treatment H) approximately 30 minutes after the start of a high-fat breakfast. The dose was swallowed with approximately 240 mL water.

A washout period of at least 6 days separated the treatment administration. In each study period, 17 blood samples for pharmacokinetic analysis were taken within 1 hour before and at 5, 10, 20, 40, 60, 80, 100 minutes, as well as at 2, 3, 4, 6, 8, 12, and 24, 36, and 48 hours after drug administration. Plasma was harvested and quantified for naproxen using a validated analytical method. Subjects were monitored to report any adverse events that may occur.

Objectives:

Part 1. To compare the bioavailability of naproxen sodium from single doses of:
    test 220 mg tablet formulation 1 relative to Aleve® 220 mg tablet in a fasted state;
    test 220 mg tablet formulation 1 relative to test 220 mg tablet formulation 2 in a fasted state; and
    test 220 mg tablet formulation 2 relative to Aleve® 220 mg tablet in a fasted state.

Part 2. To compare bioavailability of naproxen sodium from single dose of:
    test 220 mg tablet formulation 1 relative to reference products (Nalgesin S® 275 mg tablet and Aleve 220 mg Liquid Gels®) in a fasted state; and
    test 220 mg tablet formulation 2 relative to reference products (Nalgesin S® 275 mg tablet and Aleve 220 mg Liquid Gels®) in a fasted state.

Part 3. To assess potential food effects by comparing the bioavailability of naproxen sodium from single doses of:
    test 220 mg tablet formulation 1 in a fed state relative to test 220 mg tablet formulation 2 in a fed state;
    test 220 mg tablet formulation 1 in a fed state relative to Aleve® 220 mg tablet in a fed state; and
    test 220 mg tablet formulation 2 in a fed state relative to Aleve® 220 mg tablet in a fed state.

Test products, dosage, and mode of administration:
    one naproxen sodium test 220 mg tablet, formulation 1, was administered orally with approximately 240 mL water in a fasted state (Treatment A)
    one naproxen sodium test 220 mg tablet formulation 2, was administered orally with approximately 240 mL water in a fasted state (Treatment B)
    one naproxen sodium test 220 mg tablet, formulation 1, was administered orally with approximately 240 mL water in a fed state (Treatment F)
    one naproxen sodium test 220 mg tablet formulation 2, was administered orally with approximately 240 mL water in a fed state (Treatment G)

Reference product, dosage, and mode of administration:
    one Aleve® 220 mg tablet was administered orally with approximately 240 mL water in a fasted state (Treatment C)
    one Nalgesin S® 275 mg tablet was administered orally with approximately 240 mL water in a fasted state (Treatment D)
    one Aleve 220 mg Liquid Gel® capsule was administered orally with approximately 240 mL water in fasted state (Treatment E)
    one Aleve® 220 mg tablet was administered orally with approximately 240 mL water in a fed state (Treatment H)

Duration of Study: The study duration was about nine weeks, which includes duration for eligibility screening (between one and 28 days before first dose administration) and five separate treatment periods. Subjects remained at the study site for the duration of each treatment period.

Data Evaluation: Pharmacokinetic:

The following pharmacokinetic (PK) parameters were determined by means of non-compartmental analysis for each subject and treatment: Cmax (maximum plasma concentration), Tmax (time to maximum concentration), and plasma naproxen concentrations at 5, 10, 20, 40, 60, and 80 minutes (Cp5MIN Cp10MIN, Cp20MIN, Cp40MIN, Cp60MIN and Cp80MIN), $\lambda Z$ (rate constant) and $T_{half}$ (half life).

Statistical Methods

The proposed sample size calculations are for part 1 of the study. Assuming an intra-subject coefficient of variation (CV) of 13% for CMAX, a sample size of 30 subjects were provided at least 90% power to ensure the two-sided 90% confidence interval for the ratio will be between 80-125% of the reference product, should the true mean ratio of Test to Reference product be between 0.89 and 1.12. The estimate of 13% intra-subject CV was observed in previous Naproxen bioequivalence study. See Product monograph ALEVE Liquid Gels Naproxen Sodium Tablets USP 220 mg Non-steroidal anti-inflammatory drug Analgesic, Antipyretic, Bayer Inc. Consumer Care, Apr. 10, 2013. Control No. 162299; and Setiawati et al., *Bioequivalence Study with Two Naproxen Sodium Tablet Formulations in Health Subjects*, Journal of Bioequivalence & Bioavailability, 1(1): 28-33 (2009).

Analysis for Cmax, as well as the naproxen plasma concentrations at 40, 60 and 80 minutes ($Cp_{40\ min}$, $Cp_{60\ min}$, and $Cp_{80\ min}$) were as follows:

Statistical comparisons of pairs of treatment (A versus B, A versus C, B versus C) were based on log transformed (natural log) pharmacokinetic parameter data. A mixed-effect analysis of variance model that includes treatment, period, and treatment sequence as fixed effects, and subject within sequence as a random effect, were used to estimate the least squares means and intra-subject variance. Model-based 90% confidence intervals for the geometric mean ratio of Cmax corresponding to the reference.

Analysis of Plasma Samples

During each study period, blood samples (4 mL) for pharmacokinetic analysis were collected into appropriately labeled K2EDTA Vacutainer® blood collection tubes. The tube labels included the following information (at a minimum): protocol number, subject identification number, sampling time, study period, and any applicable site specific sample identification code.

Blood samples were collected before dosing (predose) and at specific times following each designated dose. The pharmacokinetic samples were collected at the exact nominal time relative to dosing. Samples collected outside of 1-minute window for postdose time points up to 60 minutes or outside of 2-minute window for time points after 60 minutes will be captured as protocol deviations. The exact time of the sample collection were noted on the source document and data collection tool (e.g. CRF).

After drawing the blood, the tube was gently inverted approximately eight times after collection and immediately placed in an ice bath for transport to a centrifuge. Samples were kept on ice and processed into plasma within 90 minutes. Any deviations regarding the pharmacokinetic blood sample and handling process were recorded on the appropriate log.

Samples were centrifuged at high speed (~1500 g revolutions per minute) for approximately 10 minutes at approximately 4° C. nominal. As soon as the centrifuge stops, the samples were returned to an ice bath. Plasma was withdrawn into two equally divided aliquots in an appropriately labeled polypropylene transfer tube (polypropylene push-cap tube) (which can hold approximately 5 mL plasma). The tubes were labeled with freezer-safe labels and/or marked by permanent marker, and the labels were filled out and affixed to the tube before placing plasma into the tube.

Samples were placed in the freezer (approximately –20° C. nominal) within 90 minutes from the time of collection and stored until shipped. The time samples were placed in the freezer will be recorded in a sample accountability record. Samples were analyzed using a validated analytical method in compliance with the standard operating procedures of the bioanalytical laboratory. The range of validated method was 0.5 μg/mL to 100.000 μg/mL.

Model for Analysis of Results

The following single-dose pharmacokinetic parameters for naproxen sodium in plasma were estimated using non-compartmental methods:

Plasma concentrations measured at 5, 10, 20, 40, 60 and 80 minutes (Cp5MIN Cp10MIN, Cp20MIN, Cp40MIN, Cp60MIN and Cp80MIN) after dose administration;

Maximum plasma concentration (Cmax);

Time to maximum concentration (Tmax);

Half-life (T½);

Elimination rate constant ($\lambda Z$)

Cmax parameters for Nalgesin S® 275 mg tablet (E) were presented with dose normalized and without dose normalized data.

Model for Analysis of Fasted and Fed States

Comparisons were assessed of potential food effects by comparing the bioavailability of naproxen sodium from single doses of:

test 220 mg tablet formulation 1(A) fasted state versus test 220 mg tablet formulation 1(F) fed state test 220 mg tablet formulation 2 (B) fasted state versus test 220 mg tablet formulation 2(G) fed state Aleve® 220 mg tablet (C) in a fasted state versus Aleve® 220 mg tablet (H) in a fed state test 220 mg tablet formulation 1(F) fed state versus test 220 mg tablet formulation 2(G) fed state test 220 mg tablet formulation 2(G) fed state versus Aleve® 220 mg tablet (H) in a fed state test 220 mg tablet formulation 1(F) fed state versus Aleve® 220 mg tablet (H) in a fed state Statistical comparisons of pairs of treatment fed versus fasted states (F versus A, G versus B, H versus C) for set 1 PK parameters were analyzed using paired t test for log transformed (natural log) pharmacokinetic parameter. 90% confidence intervals for the geometric mean ratio of Cmax corresponding to the reference treatment (F versus A, G versus B, H versus C) will be calculated in each case.

Example 2: PK and Bioequivalence Results

TABLE 1

Mean PK Parameters for Naproxen Under Fasted Condition

| | Cmax | Cp 5 min | Cp 10 min | Cp 20 min | $T_{max}$ (h)$^a$ |
|---|---|---|---|---|---|
| Formulation 1 (300 mg Sod.Bicarb) (n = 29) | 50.69 (16.7) | 6.32 (135.9) | 21.9 (81) | 44.5 (39.5) | 0.33 (0.17-2.00) |

TABLE 1-continued

Mean PK Parameters for Naproxen Under Fasted Condition

| | Cmax | Cp 5 min | Cp 10 min | Cp 20 min | $T_{max}$ (h)$^a$ |
|---|---|---|---|---|---|
| Formulation 2 (500 mg Sod.Bicarb) (n = 27) | 54.1 (16.5) | 3.69* (138.4) | 22.41 (76) | 47.16 (36.2) | 0.33 (0.17-1.00) |
| Aleve (n = 27) | 45.16 (17.6) | 0.75 (115.7) | 6.36 (78.2) | 27.11 (47.7) | 0.67 (0.67-3.00) |
| Aleve LG (n = 14) | 42.31 (26.8) | 0.48 (177.4) | 4.73 (335.6) | 13.43 (110.2) | 1 (0.20-12.00) |
| Nalgesin S (n = 14) | 53.54 (14.3) | 2.17 (163.1) | 7.86 (91.8) | 27.24 (51.3) | 0.83 (0.67-1.67) |

*w.r.t. Formulation 1 (p < 0.05). All early absorption parameters were statistically (p < 0.05) significantly different for both Formulation 1 and Formulation 2 compared to Aleve, Aleve LG and Nalgesin under fasted condition

TABLE 2

Mean PK Parameters for Naproxen Under Fed Condition

| | Cmax | $Cp_{20\ min}$ | $CP_{40\ min}$ | $CP_{60\ min}$ | $T_{max}$ (h)$^a$ |
|---|---|---|---|---|---|
| Formulation 1 (300 mg Sod.Bicarb) (n = 9) | 31.8 (11.6) | 14.29*,† (60.5) | 18.27 (54.2) | 21.85 (46.8) | 3* (0.67-4) |
| Formulation 2 (500 mg Sod.Bicarb) (n = 8) | 28.91 (17.5) | 17.49*,† (51) | 23.02 (36.6) | 24.55 (30.4) | 1.83* (1.00-6.00) |
| Aleve ® (n = 10) | 34.67 (16.3) | 5.12* (127.8) | 11.32 (118) | 15.76 (85.6) | 2.5* (0.67-4.00) |

*w.r.t. Fasted,
†w.r.t. Aleve under Fed p < 0.05

TABLE 3

Mean PK Parameters for Naproxen Under Fasted Condition

| | Cmax (ug/mL) | $Cp_{5\ min}$ (ug * h/mL) | $CP_{10\ min}$ (ug * h/mL) | $CP_{20\ min}$ (ug * h/mL) | $CP_{40\ min}$ (ug * h/mL) | $Cp_{60\ min}$ (ug * h/mL) | $CP_{80\ min}$ (ug * h/mL) | $T_{max}$ (h)$^a$ |
|---|---|---|---|---|---|---|---|---|
| Formulation 1 (300 mg Sod.Bicarb) (n = 29) | 50.69 (16.7) | 6.324 (135.9) | 21.982 (81) | 44.455 (39.5) | 42.521 (19.1) | 39.578 (14.5) | 36.95 (12.6) | 0.33 (0.17-2.00) |
| Formulation 1 (500 mg Sod.Bicarb) (n = 27) | 54.1 (16.5) | 3.69 (138.4) | 22.41 (76) | 47.16 (36.2) | 46.25 (14.1) | 40.78 (10.6) | 37.15 (11.8) | 0.33 (0.17-2.00) |
| Aleve (n = 27) | 45.16 (17.6) | 0.75 (115.7) | 6.36 (78.2) | 27.11 (47.7) | 40.84 (29.5) | 39.48 (21.4) | 38.09 (18.6) | 0.33 (0.17-1.00) |
| Aleve Liquid Gel (n = 14) | 42.31 (26.8) | 0.48 (177.4) | 4.73 (335.6) | 13.43 (110.2) | 34.43 (45.7) | 34.75 (39.3) | 34.98 (34.8) | 0.67 (0.67-3.00) |
| Nalgesin S (n = 14) | 53.54 (14.3) | 2.17 (163.1) | 7.86 (91.8) | 27.24 (51.3) | 47.74 (28.2) | 48.5 (19.6) | 47.1 (13) | 0.67 (0.17-1.00) |

TABLE 4

Summary of Time to Effective Blood Plasma Concentration

| | Time to 15-20 µg/mL* (min) | | Tmax, (min) | | Cmax (µg/mL) | |
|---|---|---|---|---|---|---|
| | Fasted** | Fed*** | Fasted | Fed | Fasted | Fed |
| Formulation 1 (300 mg Sod Bicarb) | 7-9 | 20-50 | 20 | 180 | 50.7 | 31.8 |
| Formulation 2 (500 mg Sod Bicarb) | 7-9 | 15-25 | 20 | 110 | 54.1 | 28.9 |
| Aleve (220 mg Naproxen) | 14-17 | 60-85 | 40 | 150 | 45.2 | 34.7 |
| Aleve LG (220 mg Naproxen) | 20-24 | | 60 | | 42.3 | |
| Nalgesin S 275 | 13-17 | | 50 | | 53.5 | |

Sod Bicarb: Sodium Bicarbonate

Figure 2:
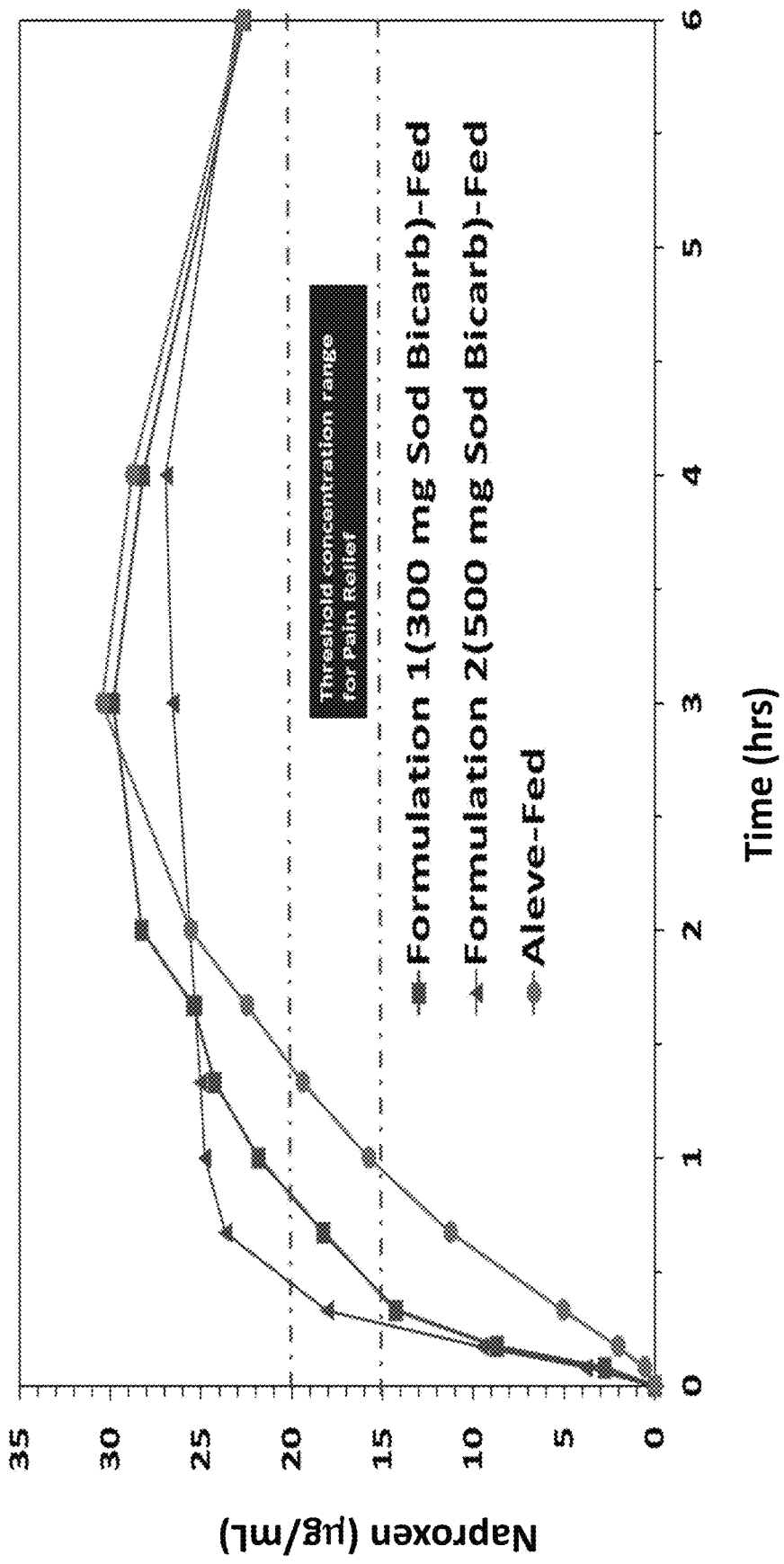
FIG. 2 depicts the mean naproxen concentration time profiles under fed conditions for the study described in Examples 1 and 2.

*15-20 µg/mL is considered the minimum effective blood plasma concentration for naproxen
**FIG. 1
***FIG. 2

Example 3: Compositions for Use in PK Study

The following formulations were prepared for use in the PK study.

TABLE 5

220 mg Naproxen Sodium, 300 mg Sodium Bicarbonate formulation (Formulation 1)

| Material | Mg/Tablet | Weight % (% w/w) |
|---|---|---|
| Intragranular | | |
| Naproxen Sodium USP | 220.00 | 26.27 |
| Microcrystalline Cellulose, NF (Avicel PH101)[1] | 50.00 | 5.97 |

TABLE 5-continued

220 mg Naproxen Sodium, 300 mg Sodium Bicarbonate formulation (Formulation 1)

| Material | Mg/Tablet | Weight % (% w/w) |
|---|---|---|
| Pregelatinized Starch, USP[2] | 16.00 | 1.91 |
| Povidone, USP (PVP K29/32)[3] | 10.00 | 1.19 |
| Crospovidone, NF[4] | 16.00 | 1.91 |
| Purified Water[5] | — | — |
| Extragranular | | |
| Sodium Bicarbonate USP | 300.00 | 35.83 |
| Crospovidone NF[4] | 63.00 | 7.52 |
| Microcrystalline Cellulose NF (Avicel PH105)[1] | 140.00 | 16.72 |
| Colloidal Silicon Dioxide NF (Aerosil 200)[6] | 4.00 | 0.48 |
| Magnesium Stearate NF | 6.00 | 0.72 |
| Tablet Coating | | |
| Film Coating Solution (Polyvinyl alcohol based)[7] | 12.40 | 1.48 |
| Water | — | — |
| TOTAL | 837.40 | 100.00 |

[1]Commercially available from the FMC Corporation as Avicel ®
[2]Commercially available from the Colorcon Corporation as Starch 1500
[3]Commercially available from the Ashland Corporation as PVP K29/32
[4]Commercially available from the BASF Corporation as Kollidon ® CL
[5]Water removed upon drying granulation
[6]Commercially available from the Evonik Corporation as Aerosil ®
[7]Commercially available from the Colorcon Corporation as Opadry ® II Granulation and Tableting Procedure (for Formulation 1 (Table 5) & Formulation 2 (Table 6)):

1. The intragranular material was added to a high shear granulator; the purified water was added.
2. The granulation was discharged from the granulator and passed through a Co-Mil for sizing and added to a fluid bed dryer.
3. The granulation was dried and again passed through a Co-Mil; and blended with the extragranular materials to form a final blend.
4. The blend was compressed into tablets at a compression force of 18-26 kilonewtons, resulting in a hardness of 10-15 kiloponds.
5. The tablets were added to a coating pan.
6. The film coating solution was sprayed onto the tablets and dried.

Physical Parameters for Intragranular Portion & Sodium Bicarbonate

Bulk Density of intragranular (granulation) portion: 0.6 g/cc±0.05
Tap Density of intragranular (granulation) portion: 0.7 g/cc±0.15
Particle Size Distribution of intragranular (granulation) via sieve analysis: 222-372 μm
Particle Size of Sodium Bicarbonate USP: 90-95 μm

TABLE 6

220 mg Naproxen Sodium, 500 mg Sodium Bicarbonate formulation (Formulation 1)

| Material | Mg/Tablet | Weight % (% w/w) |
|---|---|---|
| Intragranular | | |
| Naproxen Sodium USP | 220.00 | 20.45 |
| Microcrystalline Cellulose, NF (Avicel PH101)[1] | 50.00 | 4.65 |
| Pregelatinized Starch, USP[2] | 16.00 | 1.49 |
| Povidone, USP (PVP K29/32)[3] | 10.00 | 0.93 |
| Crospovidone, NF[4] | 16.00 | 1.49 |
| Purified Water[5] | — | — |
| Extragranular | | |
| Sodium Bicarbonate USP | 500.00 | 46.47 |
| Crospovidone NF[4] | 80.00 | 7.43 |
| Microcrystalline Cellulose NF (Avicel PH105)[1] | 154.00 | 14.31 |
| Colloidal Silicon Dioxide NF (Aerosil 200)[6] | 6.00 | 0.56 |
| Magnesium Stearate NF | 8.00 | 0.74 |
| Tablet Coating | | |
| Film Coating Solution (Polyvinyl alcohol based)[7] | 15.90 | 1.48 |
| Water[5] | — | — |
| TOTAL | 1075.90 | 100.00 |

[1]Commercially available from the FMC Corporation as Avicel ®
[2]Commercially available from the Colorcon Corporation as Starch 1500
[3]Commercially available from the Ashland Corporation as PVP K29/32
[4]Commercially available from the BASF Corporation as Kollidon ® CL
[5]Water removed upon drying granulation and coating
[6]Commercially available from the Evonik Corporation as Aerosil ®
[7]Commercially available from the Colorcon Corporation as Opadry ® II Example 3: Dissolution (In-Vitro) Results The formulations in Table 8 were tested for dissolution using a USP dissolution apparatus 2 with 900 mL of 0.0033 N hydrochloric acid at 30 rpm and 37° C. Samples were pulled at respective timepoints and analyzed via a high pressure liquid chromatography (HPLC) apparatus equipped with a Phenomenex Kinetex C18 column (50 mm×4.6 mm); with a mobile phase of 60:40 Water:Methanol plus 0.1% trifluoroacetic acid; a flow rate of 1.0 mL/min; an injection volume of 10 μL; a UV detector set at 332 nm; and a column temperature of 30° C.

TABLE 7

Dissolution in 0.0033M HCL

Dissolution (% released, Average of n = 6 vessels) Media: 0.0033M HCl, 30 RPM, USP Apparatus 2 (paddles)

| Formulation | 0 Min | 5 Min | 10 Min | 30 Min |
|---|---|---|---|---|
| Formulation 1 (300 mg Sod Bicarb) | 0 | 57 | 82 | 91 |
| Formulation 2 (500 mg Sod Bicarb) | 0 | 61 | 80 | 90 |
| Aleve (220 mg Naproxen) | 0 | 14 | 23 | 227 |
| Aleve LG* (220 mg Naproxen) | 0 | 1 | 3 | 5 |
| Nalgesin S 275 | 0 | 9 | 14 | 22 |

Min = Minutes
LG = Liquigel

The formulations in Table 8 were also tested for dissolution using a USP dissolution apparatus 2 with 900 mL of 7.4 phosphate buffer at 50 rpm and 37° C. The data is shown in Table 12. The dissolution method (media, apparatus, speed, temperature) was the same as for naproxen sodium tablets as defined by USP 41-NF 36. The method for analyzing the pulled dissolution samples was the same as those for Table 11.

TABLE 8

Dissolution in pH 7.4 phosphate buffer

Dissolution (% released, Average of n = 6 vessels)
Media: 7.4 Buffer, 30 RPM, USP Apparatus 2 (paddles)

| Formulation | 3 Min | 5 Min | 6 Min | 10 Min | 30 Min | 45 Min | 60 Min |
|---|---|---|---|---|---|---|---|
| Formulation 1 (300 mg Sod Bicarb) | 92 | 100 | | 101 | 101 | 101 | |
| Aleve (220 mg Naproxen) | 12.5 | 26.4 | | 58.2 | 95.1 | 98.9 | |
| Aleve LG* (220 mg Naproxen | 2 | | 3 | 12 | 62 | 80 | 97 |

Min = Minutes
LG = Liquigel

The invention claimed is:

1. A method of administering naproxen which consists of providing to a human in a fasted state an immediate release solid dosage form of naproxen, said solid dosage form providing a blood plasma naproxen concentration of at least 15-20 µg/ml in 10 minutes or less, wherein the solid dosage form comprises an intragranular portion and a carbonate portion, wherein the intragranular portion comprises 220 mg of naproxen sodium, as well as compression filler, binder and disintegrant, wherein the carbonate portion comprises an effective amount of soluble carbonate at a particle size from about 50 microns to 200 microns so as to raise the pH and facilitate dissolution and absorption of the naproxen to begin in the human's stomach, wherein the particle size of the intragranular portion is from about 200 microns to 400 microns, and wherein the solid dosage form does not include any other drug besides naproxen sodium.

2. A method of administering naproxen according to claim 1 wherein the dosage form provides a blood plasma naproxen concentration of at least 15-20 µg/ml in 7-9 minutes.

3. A method of administering naproxen according to claim 1 wherein the particle size of the carbonate is from about 75 microns to 100 microns.

4. A method of administering naproxen according to claim 1 wherein the amount of carbonate in the dosage form is from about 300 mg to 500 mg.

5. A method of administering naproxen according to claim 1 wherein the particle size of the intragranular portion is from about 200 microns to 300 microns.

6. A method of administering naproxen which consists of providing to a human in a fed state an immediate release solid dosage form of naproxen, said solid dosage form providing a blood plasma naproxen concentration of at least 15-20 µg/ml in 50 minutes or less, wherein the solid dosage form comprises an intragranular portion and a carbonate portion, wherein the intragranular portion comprises 220 mg of naproxen sodium, as well as compression filler, binder and disintegrant, wherein the carbonate portion comprises an effective amount of soluble carbonate at a particle size from about 50 microns to 200 microns so as to raise the pH and facilitate dissolution and absorption of the naproxen to begin in the human's stomach, wherein the particle size of the intragranular portion is from about 200 microns to 400 microns, and wherein the solid dosage form does not include any other drug besides naproxen sodium.

7. A method of administering naproxen according to claim 6 wherein the dosage form provides a blood plasma naproxen concentration of at least 15-20 µg/ml in 25 minutes or less.

8. A method of administering naproxen according to claim 6, wherein the particle size of the carbonate is from about 75 microns to 100 microns.

9. A method of administering naproxen according to claim 6, wherein the amount of carbonate in the dosage form is from about 300 mg to 500 mg.

10. A method of administering naproxen according to claim 6, wherein the particle size of the intragranular portion is from about 200 to 300 microns.

* * * * *